United States Patent [19]
Ishikawa

[11] Patent Number: 4,812,033
[45] Date of Patent: Mar. 14, 1989

[54] OPHTHALMIC APPARATUS

[75] Inventor: Yasuyuki Ishikawa, Yokohama, Japan

[73] Assignee: Canon Kabushiki Kaisha, Tokyo, Japan

[21] Appl. No.: 33,207

[22] Filed: Apr. 2, 1987

[30] Foreign Application Priority Data

Feb. 26, 1985 [JP] Japan ................... 60-036789
Apr. 11, 1986 [JP] Japan ................... 61-083462

[51] Int. Cl.$^4$ .............................................. A61B 3/14
[52] U.S. Cl. ..................... 351/208; 351/206; 354/62
[58] Field of Search ............... 351/206, 207, 208; 354/62

[56] References Cited

U.S. PATENT DOCUMENTS 4,511,227 4/1985 Nunokawa et al. ............... 351/208
4,678,297 7/1987 Ishikawa et al. ................. 351/208

FOREIGN PATENT DOCUMENTS

51-69629 6/1976 Japan .
58-22026 2/1983 Japan .

Primary Examiner—Rodney B. Bovernick
Attorney, Agent, or Firm—Fitzpatrick, Cella, Harper & Scinto

[57] ABSTRACT

An ophthalmic apparatus has an objective optical system opposed to an eye to be examined. First and second photodetectors are provided on the substantially conjugate plane of the iris of the eye to be examined with respect to the objective optical system when the operating distance to the eye to be examined is appropriate. The photodetectors detect the image of the iris of the eye to be examined and the image of the pupil of the eye to be examined, respectively, and a detecting device compares the output of the first and second photodetectors and detects the state of alignment with the eye to be examined.

19 Claims, 7 Drawing Sheets

OPHTHALMIC APPARATUS

CROSS REFERENCE

This application is a continuation-in-part of application Ser. No. 831,585 filed Feb. 21, 1986, now abandoned.

BACKGROUND OF THE INVENTION

1. Field of the Invention

This invention relates to an ophthalmic apparatus capable of detecting the state of alignment of an eye to be examined.

2. Description of Related Art

When an ophthalmic apparatus is to be used, for example, when the fundus of an eye to be examined is to be photographed by an eye fundus camera or when the refractive power of an eye is to be measured by an eye refractometer, it is important in achieving an exact and highly accurate examination or measurement to properly carry out the alignment adjustment for aligning the optic axis of the eye examining instrument with the visual axis of the eye to be examined, and the operation of making the operating distance between the eye to be examined and the eye examining instrument coincident with an optimum value.

Numerous means for carrying out the alignment adjustment and the operating distance adjustment have already been proposed. Many of those propositions utilize the fact that the surface of the cornea of the eye to be examined has a function corresponding to a convex mirror. In the case of this method, the eye examining instrument can be adjusted so that the optic axis thereof passes through the vertex of the cornea. It is not always ensured that the optic axis will pass through the center of the pupil because there is an individual difference in the positional relation between the cornea and the pupil.

Accordingly, depending on the eye to be examined, an error in examination or measurement occurs and reduces the accuracy of examination or measurement. Also, where the convex mirror function of the surface of the cornea is utilized, if the reflected light from the cornea varies greatly in conformity with the state of alignment due to the radius of curvature of the cornea being small and the tolerance within which the reflected light from the cornea can be detected for the detection of the state of alignment is so small that the positional relation between the eye to be examined and the ophthalmic apparatus is generally incoincident, it has been impossible to detect the positional information of the eye to be examined.

Further, when the eye to be examined is to be photographed or measured by an eye fundus camera or an eye refractometer, photographing, photographing or measurement cannot be accomplished unless the diameter of the pupil of the eye to be examined is open over a predetermined value. Heretofore, the examiner has judged by seeing the image in the viewfinder or on the TV monitor. But this leads to a disadvantage of requiring an experienced examiner. Also, where the diameter of the pupil of the eye to be examined is somewhat greater than a predetermined value, photographing or measurement can be accomplished, but the adjustment of the alignment with the eye to be examined must be strict and in this respect requires attentiveness by the examiner.

SUMMARY OF THE INVENTION

It is an object of the present invention to provide an ophthalmic apparatus in which, independently of the positional relation between the cornea and pupil of an eye to be examined, accurate alignment can be accomplished in a direction perpendicular to the optic axis and also in the direction of the optic axis.

It is also an object of the present invention to provide an ophthalmic apparatus which is capable of detecting the state of alignment even if an eye to be examined greatly deviates from a regular position in a direction perpendicular to the optic axis.

An ophthalmic apparatus according to the present invention has an objective optical system opposed to an eye to be examined; first and second photodetectors provided on the substantially conjugate plane of the iris of the eye to be examined with respect to said objective optical system when the operating distance to the eye to be examined is appropriate, said first and second photodetectors detecting the image of the iris of the eye to be examined and the image of the pupil of the eye to be examined, respectively; and detecting means for comparing the outputs of said first and second photodetectors to detect the state of alignment with the eye to be examined.

DESCRIPTION OF THE PREFERRED EMBODIMENTS

Figure 1:
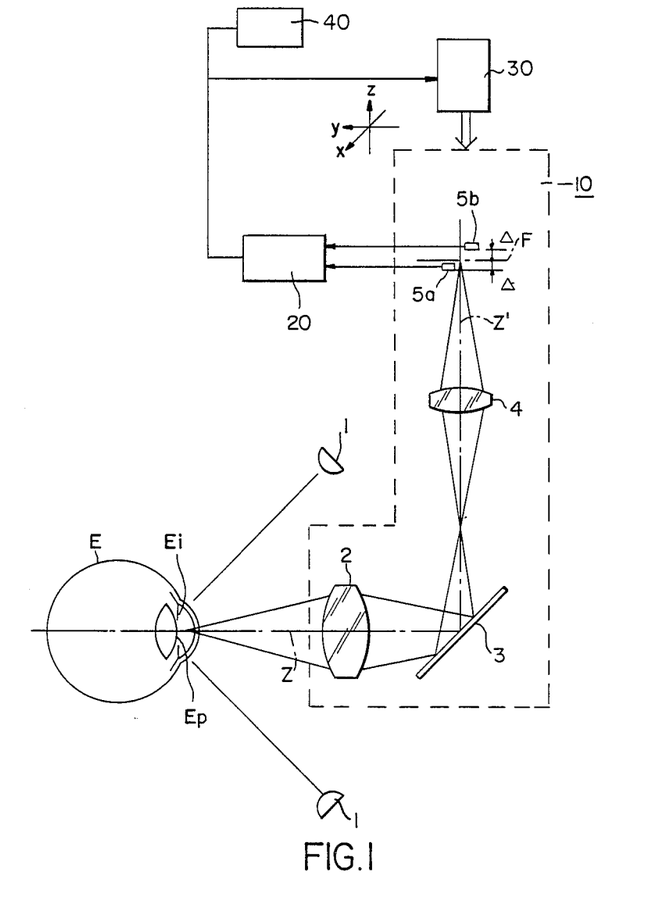
FIG. 1 shows the construction of a first embodiment of the present invention.

Referring to FIG. 1, letter E designates an eye to be examined, and at least one light source 1 for illuminating the eye to be examined is disposed obliquely above the eye to be examined. An objective 2 is provided in opposed relationship with the eye E to be examined, an optical path bending mirror 3 is disposed behind the objective 2, and a relay lens 4 and line sensors 5a and 5b each comprising, for example, a CCD (charge coupled device) are successively arrayed along an optic axis Z' bent from an optic axis Z by the optical path bending mirror 3.

The line sensors 5a and 5b are disposed parallel to each other so that the distance therebetween corresponds to the distance between the left and right eyes of the examinee, i.e., the horizontal direction. Such a conjugate relation is established that when the operating distance between the iris Ei of the eye E to be examined and the eye examining instrument is proper, the image of the iris Ei is formed on a plane F between the line sensors 5a and 5b set at an interval 2Δ in the direction of the optic axis.

Reference numeral 20 designates a detecting circuit for comparing the outputs of the line sensors 5a and 5b and detecting the aligned state of the eye to be examined. Reference numeral 30 denotes driving means for driving a body 10 in x, y and z directions on the basis of the output of the detecting circuit 20, and reference numeral 40 designates a display device for displaying the aligned state of the eye to be examined by a numerical value or an arrow.

Figure 2:
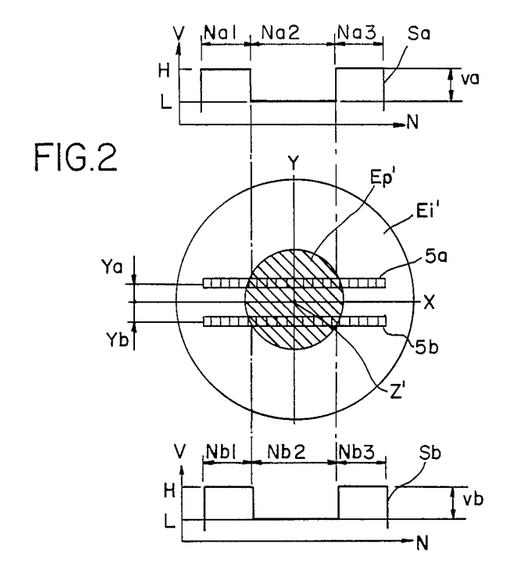
FIG. 2 illustrates the output wave forms of line sensor and the image of an eye to be examined in a state in which alignment adjustment and operating distance adjustment are correct.

FIG. 2 is a plan view taken along a plane perpendicular to the optic axis Z' and showing the positional relation between the image of the iris Ei of the eye E to be examined formed on the plane F by the line sensors 5a, 5b, the objective 2 and the relay lens 4 and the image of the pupil Ep of the eye E to be examined. The length of the line sensors 5a and 5b is sufficiently longer than the photographed image Ep' of the pupil. Ei' designates the image of the iris Ei, and Ep' denotes the image of the pupil Ep. The image Ei' of the iris is light and the image Ep' of the pupil is dark. Sa and Sb are the schematic output wave forms of the outputs of the line sensors 5a and 5b, respectively.

FIG. 2 shows the state when the eye E to be examined and the eye examining apparatus have been properly aligned. The line sensors 5a and 5b are disposed so that the output wave forms Sa and Sb are symmetrical in X and Y directions and orthogonal to the optic axis Z' when the eye E to be examined and the eye examining apparatus have been properly aligned. That is, the optic axis Z' and the center of the image Ep' of the pupil are coincident with each other, and the spacings Ya and Yb between the optic axis Z' and the respective line sensors 5a and 5b are equal to each other. The image of the eye E to be examined is projected onto the line sensors 5a and 5b, and in conformity with the light and darkness by the iris image Ei' and the pupil image Ep', the outputs Sa and Sb of the line sensors 5a and 5b become symmetrical. That is, high at the opposite ends and low at the central portion. Here, the alignment is properly done both vertically and horizontally and therefore, the widths of the H level portions of the outputs Sa and Sb are equal to each other. That is, $Na1 = Na3 = Nb1 = Nb3$, and the widths of the L level portions of the outputs Sa and Sb are also equal to each other, that is, $Na2 = Nb2$. Also, the light-recieving surfaces of the line sensors 5a and 5b are spaced apart from each other by an equal distance with respect to the optically conjugate plane F of the iris Ei and therefore, the images formed on the plane F are projected onto the line sensors 5a and 5b while being, somewhat blurred by an equal amount and the differences Va and Vb between the H level portions and the L level portions of the outputs Sa and Sb become equal to each other.

Figure 3:
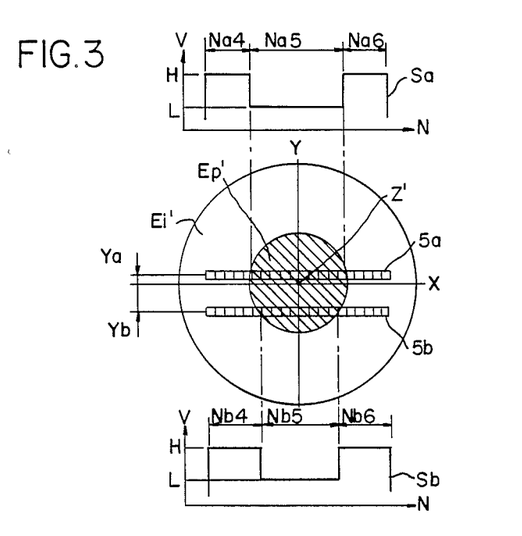
FIGS. 3 and 4 illustrate a state in which alignment adjustment is bad.

As an example of the case where alignment has not been properly effected, description will now be made of a case where the eye E to be examined and the eye examining apparatus deviate vertically from each other as shown in FIG. 3. In this case, the optic axis Z' and the center of the pupil image of Ep' deviate from each other, and the spacings between the center of the pupil image Ep' and the respective line sensors 5a, 5b and $Ya \neq Yb$. At this time, the widths of the H level portions and the L level portions of the outputs of the line sensors 5a and 5b are $Na4 = Na6 \neq Nb5 = Nb6$ and $Na5 \neq Nb5$, respectively. If from this state, vertical alignment adjustment is effected so that $Na5 = Nb5$, a properly aligned state will occur.

Figure 4:
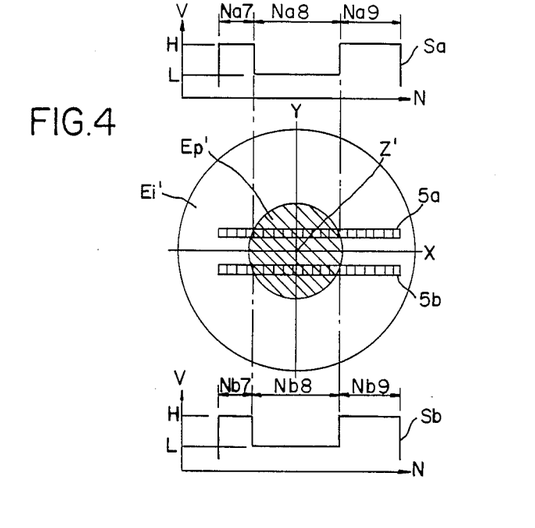

FIG. 4 shows a case where the eye E to be examined and the apparatus deviate horizontally from each other, and the pupil image Ep' is projected while being offset lengthwise from the line sensors 5a and 5b. Accordingly, the widths of the H level portions and the L level portions of the outputs of the line sensors 5a and 5b are $Na7 \neq Na9$, $Nb7 \neq Nb9$, $Na7 = Nb7$, $Na9 = Nb9$ and $Na8 = Nb8$. If from this state, horizontal alignment adjustment is effected so that $Na7 = Na9 = Nb7 = Nb9$, a properly aligned state will be brought about.

Figure 5:
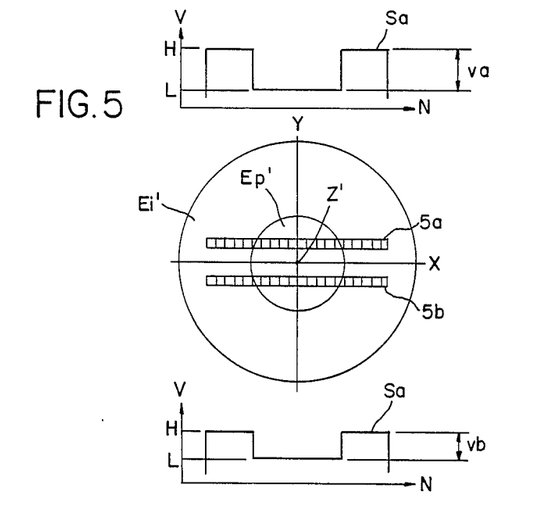
FIG. 5 illustrates a state in which operating distance adjustment is bad.

FIG. 5 shows a case where the operating distance between the eye E to be examined and the apparatus in the longitudinal direction is improper. In this case, the image Ei' of the iris and the image Ep' of the pupil, of the eye E to be examined are formed not on the plane F in FIG. 1 but forwardly or rearwardly of the plane F and therefore, the imaged state differs between the line sensors 5a and 5b and a difference occurs in the contrast of light and darkness. Accordingly, the differences between the H level portions and the L level portions of the outputs of the line sensors 5a and 5b are $va \neq vb$. If from this state, operating distance adjustment is effected so that $va = vb$, a proper operating distance will be obtained.

If, in FIG. 1, the line sensors 5a and 5b are arranged on the same plane, only the two-dimensional detection of a component perpendicular to the optic axis will become possible.

Figures 6, 7, 8:
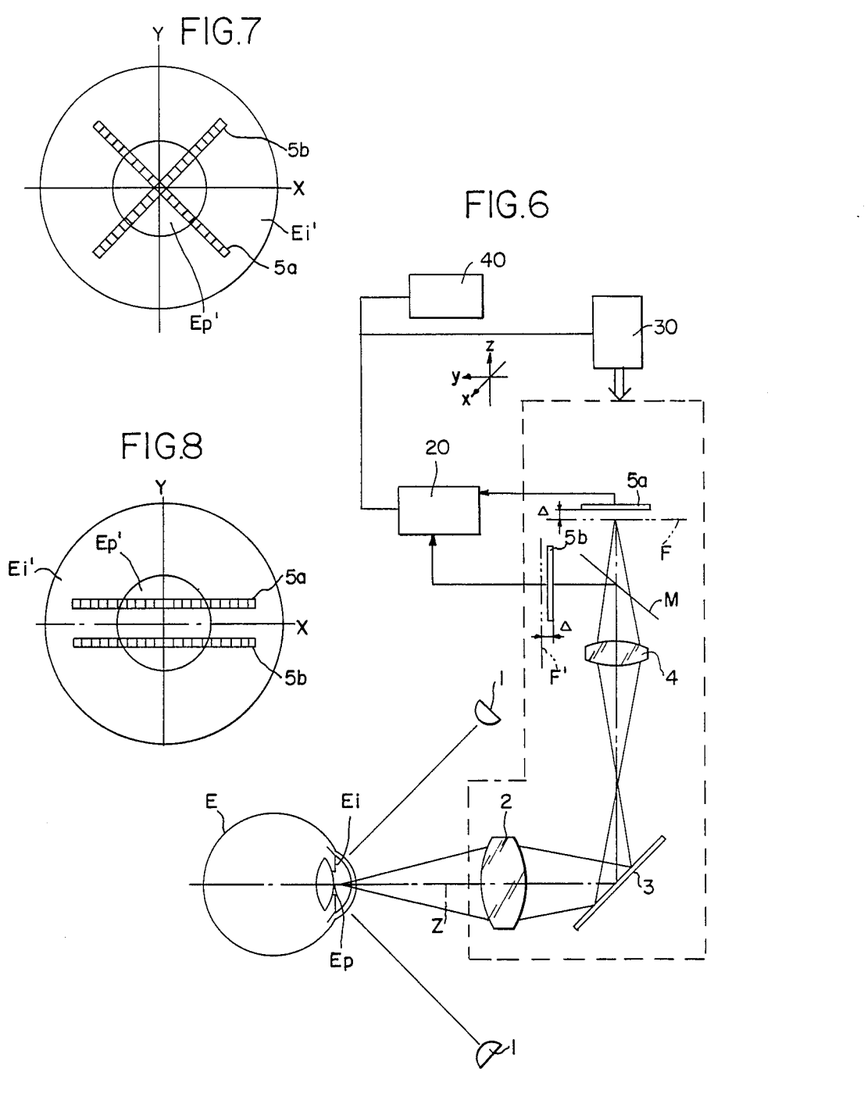
FIG. 6 shows the construction of a second embodiment of the present invention.
FIG. 7 shows the relation of the disposition between two line sensors.
FIG. 8 shows a different relation of the disposition between the two line sensors in the embodiment of FIG. 6.

FIGS. 6 and 7 show a second embodiment of the present invention. In FIGS. 6 and 7, reference numerals similar to those in FIG. 1 designate similar members. In FIG. 6, optical paths leading to planes F and F' conjugate with the iris Ei of the eye to be examined when the operating distance to the eye to be examined is appropriate are formed by a beam splitter M. It is to be understood that the quantity of light transmitted through the beam splitter M and the quantity of light reflected by the beam splitter M are equal to each other.

The line sensor 5a and the line sensor 5b are provided at a position rearward of the conjugate plane F' by an amount Δ, respectively, so as to be orthogonal to each other when projection is effected onto the side of the eye to be examined.

In order to prevent the obstruction of the detecting light by eyelashes or the like of the eye to be examined, the line sensors 5a and 5b are disposed at a predetermined angle, for example, an angle of 45° as shown in FIG. 7, with respect to the direction linking the left and right eyes of the examinee, i.e., the horizontal direction. Alternatively, as shown in FIG. 8, the two line sensors may be disposed in the two optical paths formed by the beam splitter M, in parallel with the horizontal direction. If, in FIG. 6, the line sensors 5a and 5b are disposed on the conjugate planes F and F', respectively, only the two-dimensional detection of a component perpendicular to the optic axis will become possible.

Figure 9:
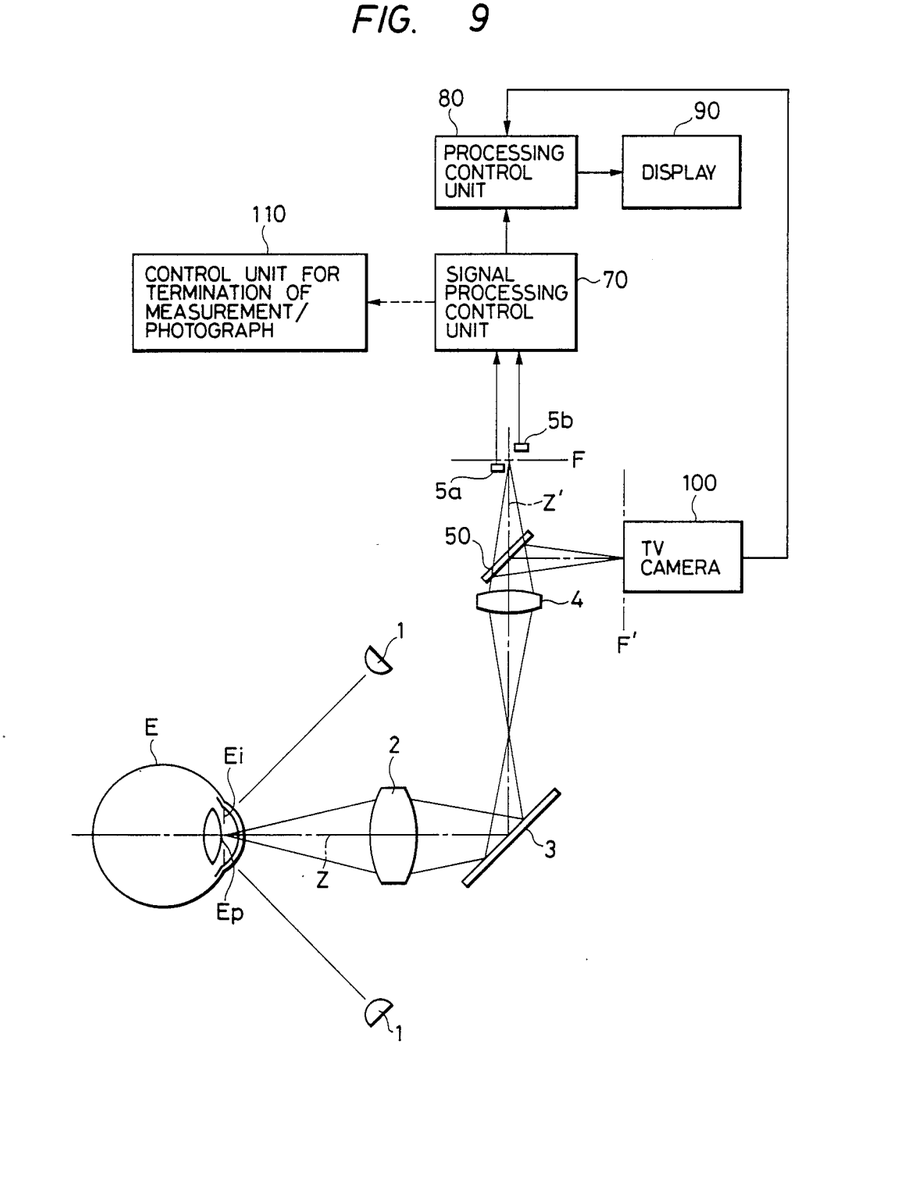
FIG. 9 shows a third embodiment.

A third embodiment will now be shown. In FIG. 9, reference characters similar to those in FIG. 1 designate similar members. In FIG. 9, reference numeral 70 designates a signal processing control unit adapted to drive the line sensors 5a and 5b, sample, amplify and waveform-shape the outputs of the line sensors 5a and 5b, A/D-convert said outputs and deliver them into a processing control unit 80. The outut of the processing control unit 80 is put out to a display unit 90 such as a CRT. On the other hand, a TV camera 100 is disposed on a plane F′ conjugate with the plane F on the reflection side of a beam splitter 50 (comprising a half-mirror, for example), and the video signals of the TV camera 100 are adapted to be delivered into the display unit 90 via the processing control unit 80.

To accomplish alignment correctly, as previously described, alignment adjustment in the vertical direction is effected so that Na5=Nb5 as shown in FIGS. 3, 4 and 5 and alignment adjustment in the left-to-right direction is effected so that Na7=Na9=Nb7=Nb9, and further, adjustment in the direction of the optic axis is effected so the differences Va and Vb between the H level portions and the L level portions of outputs Sa and Sb are equal to each other.

Here, as an example of the case where alignment has not been effected correctly, description is made of a case where the eye E to be examined and the eye examining apparatus deviate from each other with respect to the vertical direction as shown in FIG. 3. In this case, the optic axis Z′ and the center of pupil image Ep′ deviate from each other, and the intervals between the center of the pupil image Ep′ and the line sensors 5a and 5b are Ya≠Yb. At this time, the widths of the H level and L level portions of the outputs of the line sensors 5a and 5b are Na4=Na6≠Nb4=Nb6 and Na5≠Nb5, respectively.

Here, an attempt is made to find the diameter of the pupil Ep on the assumption that the pupil image Ep′ is circular. The radius of the pupil image Ep′ is r, and Ya+Yb is a predetermined constant. As an example, said diameter can be calculated by $$2r = \{1/(Ya + Yb)\} \cdot (\{(Nb5/2)^2 - (Na5/2)^2 - (Ya + Yb)^2\}^2 + 4(Ya + Yb)^2 \cdot (Nb5/2)^2)^{\frac{1}{2}}$$

The projection magnification of the pupil image Ep′ and the picture element pitches of the line sensors 5a and 5b are known and therefore, if the diameter of the pupil image Ep′ found from above equation is multiplied by a predetermined magnification, the diameter of the pupil Ep of the eye E to be examined can be calculated. When the radius r of the pupil image Ep′ is found, the intervals Ya and Yb are now found and the amount of deviation between the center of the pupil Ep and the optic axis Z′ can be calculated. As an example, the following equations are derived:

$$Ya = \pm\{r^2 - (Na5/2)^2\}^{\frac{1}{2}}$$

$$Yb = \pm\{r^2 - (Nb5/2)^2\}^{\frac{1}{2}}$$

Here, Ya<>(Ya+Yb), Yb<>(Ya+Yb) and Ya<>Yb are determined, and the amount of deviation δy when(Ya or Yb)<Ya+Yb and Ya<Yb is found from δy=(Ya+Yb)/2−Ya, and since Ya<Yb with respect to the direction, it is seen that the center of the pupil deviates upwardly from the optic axis Z′. The amount of deviation δy′ when Yb>(Ya+Yb) is found from δy′=(Ya+Yb)/2+Ya. In this manner, the amount of deviation between the center of the pupil image Ep′ and the optic axis Z′ can be calculated, and the amount and direction of deviation of the alignment can be found from the projection magnification of the pupil image Ep′ and the picture element pitches of the line sensors 5a and 5b.

FIG. 4 shows a case where the eye E to be examined and the apparatus deviate with respect to the horizontal direction, and the pupil image Ep′ is projected more toward the lengthwise direction of the line sensors 5a and 5b. Accordingly, the widths of the H level and L level portions of the outputs of the line sensors 5a and 5b are Na7≠Na9, Nb7≠Nb9, Na7=NB7, Na9=Nb9 and Na8=Nb8. Here, the amount of deviation δx in the left-to-right direction is $$\begin{aligned}\delta x &= (Na7 + Na8 + Na9)/2 - \{Na7 + (Na8/2)\} \\ &= (Nb7 + Nb8 + Nb9)/2 - \{Nb7 + (Nb8/2)\}\end{aligned}$$

whereby the amount of deviation δx can be simply found by multiplying it by a predetermined magnification as previously described.

FIG. 5 shows a case where the working distance between the eye E to be examined and the apparatus, i.e., the back-to-forth direction, is improper. In such case, the iris image Ei′ and pupil image Ep′ of the eye E to be examined are not formed on the plane F in FIG. 1 but are formed forwardly or rearwardly of the plane F and therefore, the imaged condition differs between the line sensors 5a and 5b and a difference is produced in the contrast of light and shade. Thus, the differences between the H level and L level portions of the outputs of the line sensors 5a and 5b are va≠vb. When va−vb is determined, the direction of deviation can be known, and the processing control unit 80 is caused to pre-store how va and vb are varied by a variation in the working distance, whereby the amount of deviation of the working distance can be found.

Figure 10:
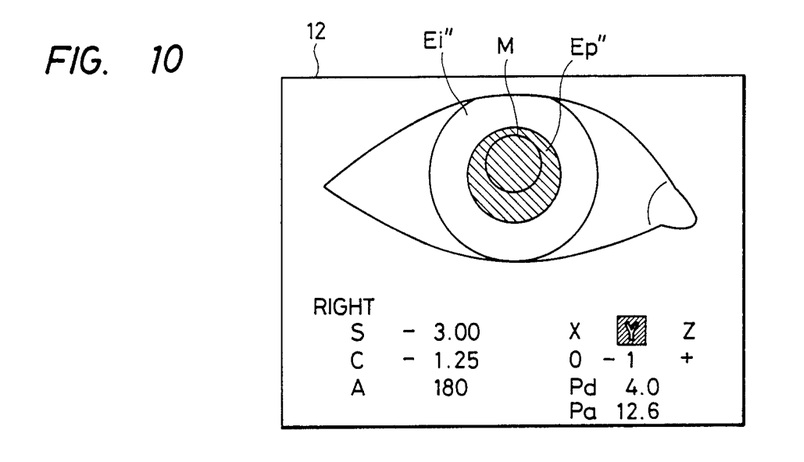
FIGS. 10 and 11 illustrate the display.

In the manner described above, the state of alignment between the eye E to be examined and the apparatus and the pupil diameter and pupil area of the eye to be examined can be calculated, and in example of the display when these are applied to an eye refractometer will now be shown. FIG. 10 shows the screen of the CRT display unit 90 on which are displayed the iris image Ei″ and pupil image Ep″ of the eye E to be examined which are the images by the TV camera 100 and a reference index mark M concentric with the optic axis Z′ of the image-synthesized apparatus. The lower half of the screen is a data display portion, letters S,C and A on the left-hand side represent the measured refraction values; X, Y and Z are displayed as alignment information on the right-hand side, X representing the left-to-right direction, Y representing the vertical direction, and Z representing the depth direction. X=0 represents that left to right is right, and in Y=−1, letter "Y" is reversed to warn that the pupil Ep of the eye E to be examined deviates by 1 mm below the optic axis Z′ of the apparatus and moreover there is an influence on the measurement accuracy. Z=+means that the working distance is too long. Pd=4.0 below the positional information means that the pupil diameter of the eye E to be examined is 4.0 mm, and Pa=12.6 means that the area of the pupil Ep is 12.6 mm².

Figure 11:
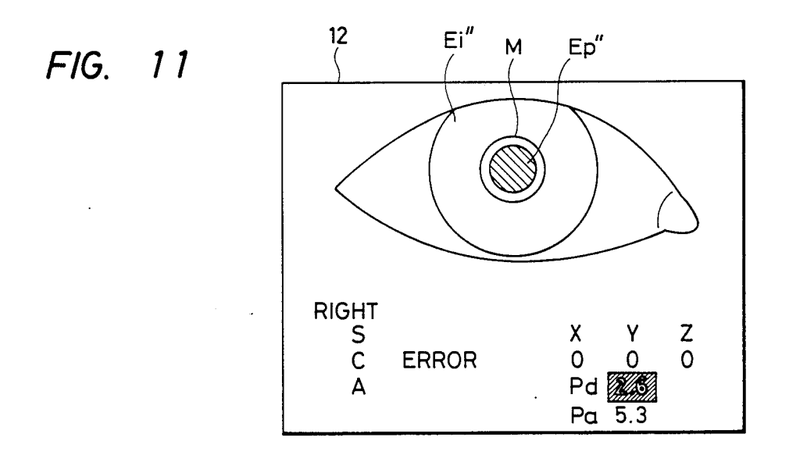

On the other hand, FIG. 11 shows a display similar to FIG. 10, and in this display, the numeral "2.6" is reversed to warn that the alignment of X, Y and Z is right but the diameter of the pupil Ep is 2.6 mm which is less than the required diameter and thus measurement is impossible, and the word ERROR in the left column of the measured refraction value also means that measurement is impossible.

In the present embodiment, the positional information of the eye E to be examined and the information of the pupil Ep cannot be measured unless the pupil image Ep' of the eye E to be examined lies on the two line sensors 5a and 5b, but if more, e.g., four line sensors are arranged on the detecting surface, the range of measurement can be widened. Also, in the present embodiment, the line sensors 5a and 5b are arranged forwardly and rearwardly, respectively, of the plane conjugate with the pupil Ep, but the beam splitter 50 may be inserted forwardly of the line sensors 5a and 5b so as to divide the light beam from the eye E to be examined and form a plurality of planes conjugate with the pupil Ep, and the line sensors 5a and 5b may be arranged in a row on the same detecting surface to accomplish detection.

Figure 12:
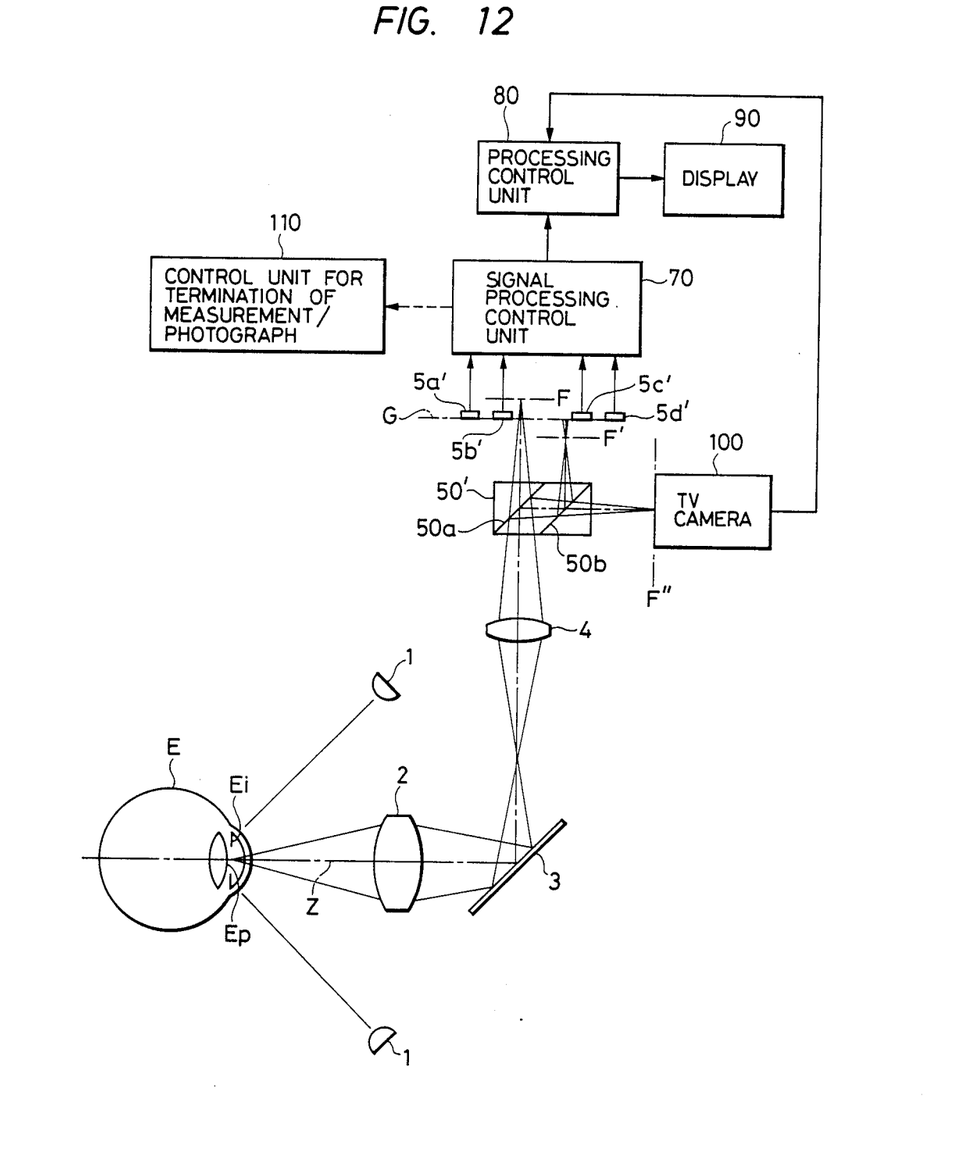
FIG. 12 shows a fourth embodiment.

FIG. 12 shows another embodiment of the present invention. A beam splitter 50' has a ⅓ transmission half-mirror surface 50a and a ½ transmission half-mirror surface 50b, and divides the light beam from the eye E to be examined and forms planes F, F' and F" conjugate with the pupil of the eye E to be examined. Line sensors 5a', 5b', 5c' and 5d' are arranged on an image detecting surface G lying intermediate of the conjugate planes F and F'. The outputs of the respective line sensors 5a', 5b', 5c' and 5d' are input to a processing control unit 80 through a signal processing control unit 70, and in the processing control unit 80, two sets of inputs may be suitably selected from four sets of input signals and operated.

Also, in this embodiment, four individual line sensors 5a', 5b', 5c' and 5d' are arranged on the image detecting surface G, but unlike the embodiment of FIG. 1, the image detecting surface is provided by a common surface and therefore, it is also possible to dispose a two-dimensional area sensor on the image detecting surface G, and this area sensor may be scanned to select any line and effect the subsequent signal processing.

Further, in the present embodiment, the conjugate planes F and F' are formed by the beam splitter 50', but if the half-mirror surfaces of the beam splitter 50' are further increased to increase the conjugate planes and correspondingly the line sensors are increased, more detailed detection will also be possible with respect to the direction of depth. In the display of the present embodiment, the positional information X, Y and Z and the pupil diameter are numerically shown, but alternatively, these can of course be coded so as to display the meanings "measurement impossible ... alignment", "measurement impossible ... small pupil", "be careful of alignment deviation", etc.

Also, in FIG. 9, reference numeral 110 designates a control unit for termination of measurement or photographing which terminates the measuring or photographing function of the ophthalmic apparatus by the output of the signal processing control unit 70. That is, it terminates the measuring or photographing function of the ophthalmic apparatus when the diameter of the pupil of the eye to be examined is smaller than a predetermined value or when the amount of deviation between the pupil of the eye to be examined and the objetive optical system is greater than a predetermined value.

Also, when the diameter of the pupil of the eye to be examined is greater than the predetermined value, the allowable amount of deviation between the pupil of the eye to be examined and the objective optical system may be made variable in conformity with the diameter of the pupil, from the diameter of the pupil and said predetermined allowable amount of deviation between the pupil of the eye to be examined and the objective optical system, and when the amount of deviation between the pupil of the eye to be examined and the objective optical system exceeds the allowable amount, the display on the TV camera and the measuring or photographing function of the ophthalmic apparatus may be terminated.

It is apparent that the TV camera 100 is used for the observation of the front eye portion, but television scanning lines (e.g. two lines) may be used instead of the line sensors 5a and 5b, for alignment.

In the foregoig description, the line sensors have been shown as photodetectors, but it is apparent that a two-dimensional sensor may be used in the embodiment of FIG. 6.

Also, in the embodiments illustrated, the light source 1 for illuminating the eye to be examined has been shown, but this may be replaced by an ordinary illuminating system used in the room.

As described above, the display unit for observing the eye to be examined in the ophthalmic instrument according to the present invention has an advantage that it can detect the direction and amount of two-dimensional or three-dimensional deviation thereof such as vertical, left to right and back to forth with respect to the eye to be examined, and can also calculate the diameter and area of the pupil as required and, when for the photographing or measurement of the eye to be examined by the ophthalmic instrument, alignment is so much out of order that the photographing or measurement is impossible or is adversely affected or when the pupil of the eye to be examined is small, it can display to that effect and give the examiner warning to thereby enable correct alignment, thus improving the accuracy of the photographing or measurement and eliminating the necessity of effecting useless photographing or measurement for the small pupil.

I claim:

1. An ophthalmic apparatus having:
   an objective optical system having an optical axis and being opposed to an eye to be examined;
   first and second photodetectors provided on a substantially conjugate plane of an iris of the eye to be examined with respect to said objective optical system when the operating distance to the eye to be examined is appropriate, said first and second photodetectors detecting the image of an inner edge of the iris; and
   detecting means for comparing the outputs of said first and second photodetectors to detect the state of alignment with the eye to be examined, wherein said first and second photodetectors are disposed at a predetermined interval in the direction of the optical axis, and the conjugate plane of the iris with respect to said objective optical system is coincident with an intermediate plane between light-receiving surfaces of said first and second photodetectors when the operating distance to the eye to be examined is appropriate.

2. An ophthalmic apparatus according to claim 1, wherein said first and second photodetectors are line sensors.

3. An ophthalmic apparatus according to claim 2, wherein said first and second line sensors are disposed parallel to each other.

4. An ophthalmic apparatus according to claim 3, wherein said first and second line sensors are disposed so that a lengthwise direction thereof is substantially parallel to a reference line connecting the left and right eyes of the examinee.

5. An ophthalmic apparatus according to claim 3, wherein one of said first and second photodetectors is disposed on one side of the optical axis and said other photodetector is disposed on the other side of the optical axis.

6. An ophthalmic apparatus according to claim 1, wherein said first and second photodetectors are provided in optical paths provided by a beam splitter provided in an optical path.

7. An ophthalmic apparatus according to claim 6, wherein said first and second photodetectors are line sensors.

8. An ophthalmic apparatus according to claim 7, wherein said first and second line sensors are disposed so as to be orthogonal to each other.

9. An ophthalmic apparatus according to claim 6, wherein said first and second line sensors are disposed so that the lengthwise direction thereof corresponds to a direction forming an angle of 45° with respect to a reference line connecting the left and right eyes of the examinee.

10. An ophthalmic apparatus having:
an objective optical system having an optical axis and being opposed to an eye to be examined;
first and second photodetectors provided on a substantially conjugate plane with an iris of the eye to be examined with respect to said objective optical system when an operating distance to the eye is appropriate, said first and second photodetectors detecting the image of an inner edge of the iris; and
detecting means for comparing outputs of said first and second photodetectors to detect the state of alignment with the eye to be examined and the diameter of the pupil of the eye to be examined, wherein said first and second photodetectors are disposed at a predetermined interval in the direction of the optical axis, and the conjugate plane of the iris with respect to said objective optical system is coincident with an intermediate plane between light-receiving surfaces of said first and second photodetectors when the operating distance to the eye to be examined is appropriate.

11. An ophthalmic apparatus according to claim 10, wherein said first and second photodetectors are line sensors.

12. An ophthalmic apparatus according to claim 10, further provided with a television camera having its image receiving surface located at a position substantially conjugate with the iris of the eye to be examined.

13. An ophthalmic apparatus according to claim 12, wherein the result of the detection by said detecting means is displayed on said television camera with the image of the iris.

14. An ophthalmic apparatus according to claim 12, wherein the information of the alignment is displayed on said television camera on the basis of the output of said detecting means.

15. An ophthalmic apparatus according to claim 12, wherein warning is displayed on said television camera when the diameter of the pupil of the eye to be examined is smaller than a predetermined value.

16. An ophthalmic apparatus according to claim 10, wherein the measuring or photographing function of said ophthalmic apparatus is terminated when the diameter of the pupil of the eye to be examined is smaller than a predetermined value.

17. An ophthalmic apparatus according to claim 12, wherein warning is displayed on said television camera when the amount of deviation between the pupil of the eye to be examined and said objective optical system is greater than a predetermined value.

18. An ophthalmic apparatus according to claim 10, wherein the measuring or photographing function of said ophthalmic apparatus is terminated when the amount of deviation between the pupil of the eye to be examined and said objective optical system is greater than a predetermined value.

19. An ophthalmic apparatus according to claim 12, wherein the allowable amount of deviation between the pupil of the eye to be examined and said objective optical system is made variable in conformity with the diameter of the pupil when the diameter of the pupil of the eye to be examined is greater than a predetermined value, and the display on said television camera and the measuring or photographing function of said ophthalmic apparatus are terminated when the amount of deviation between the pupil of the eye to be examined and said objective optical system exceeds the allowable amount.

* * * * *

UNITED STATES PATENT AND TRADEMARK OFFICE
CERTIFICATE OF CORRECTION

PATENT NO. : 4,812,033
DATED : March 14, 1989
INVENTOR(S) : YASUYUKI ISHIKAWA

It is certified that error appears in the above-identified patent and that said Letters Patent is hereby corrected as shown below:

ON THE TITLE PAGE

Between [30] and [51]

Insert -- [62] Related U.S. Application Data Continuation-in-Part of application Serial No. 831,585 filed February 21, 1986, now abandoned. --.

COLUMN 1

Line 56, "photographing" (second occurrence) should be deleted.

COLUMN 3

Line 54, "being," should read -- being --.
    Line 55, "amount" should read -- amount, --.
    Line 68, "Na4=Na6≠Nb5=Nb6" should read -- Na4=Na6≠Nb4=Nb6 --.

COLUMN 4

Line 67, "outut" should read -- output --.

COLUMN 6

Line 35, "in" should read -- an --.

COLUMN 7

Line 58, "obje-" should read -- objec- --.

UNITED STATES PATENT AND TRADEMARK OFFICE
CERTIFICATE OF CORRECTION

PATENT NO. : 4,812,033

DATED : March 14, 1989

INVENTOR(S) : YASUYUKI ISHIKAWA

It is certified that error appears in the above-identified patent and that said Letters Patent is hereby corrected as shown below:

COLUMN 8

Line 11, "foregoig" should read -- foregoing --.

COLUMN 9

Line 11, "provided" should read -- divided --.

Signed and Sealed this

Eighth Day of June, 1993

Attest:

MICHAEL K. KIRK

Attesting Officer

Acting Commissioner of Patents and Trademarks